United States Patent [19]

Egger

[11] 4,054,049
[45] Oct. 18, 1977

[54] THERMAL EXTENSOMETER

[75] Inventor: Richard Egger, Bellevue, Wash.

[73] Assignee: The Boeing Company, Seattle, Wash.

[21] Appl. No.: 696,021

[22] Filed: June 14, 1976

[51] Int. Cl.² ............................................. G01N 25/16
[52] U.S. Cl. ..................................... 73/16; 73/88.5 R
[58] Field of Search ........................ 73/16, 88.5, 15.6;
33/147 D, 148 D

[56] References Cited

U.S. PATENT DOCUMENTS

| 1,638,425 | 8/1927  | Whittemore      | 33/147 |
| 2,559,789 | 7/1951  | Peckham         | 73/16  |
| 2,656,712 | 10/1953 | Comstock        | 73/16  |
| 2,734,276 | 2/1956  | Weaver          | 33/148 |
| 2,969,710 | 1/1961  | Zibritosky et al. | 73/16 |
| 3,680,357 | 8/1972  | Closener        | 73/16  |
| 3,852,672 | 12/1974 | Nelson          | 73/88.5 |

OTHER PUBLICATIONS

Loubser et al. "An Apparatus for Determining the Coefficient of Thermal Expansion of Rocks, Mortar & Concrete" in Magazine of Concrete Res. vol. 24, No. 79, 6/72 pp. 97–100.

*Primary Examiner*—Herbert Goldstein
*Attorney, Agent, or Firm*—Wolf, Greenfield & Sacks

[57] ABSTRACT

The device employs an electrical transducer for measuring thermal deformation in a specimen with a high degree of resolution. The device basically comprises a link which linearly spans the specimen in the direction and at the location in which the deformation is to be measured, and a displacement sensor with a broad temperature range such as a capacitance-based linear displacement sensor. The link is fixed to the specimen at one end and free at the other end. The link is constructed with negligible thermal expansion such as by selecting a material for the link that has a very low thermal coefficient of expansion. In one embodiment the link is constructed in two different length sections each having a different thermal expansion coefficient with the sections extending in opposite directions to provide an effective or resultant expansion that is negligible with temperature change. In another embodiment part of the sensor is supported by a frame having a higher thermal expansion coefficient than the coefficient of the link which is a single section link.

14 Claims, 3 Drawing Figures

THERMAL EXTENSOMETER

BACKGROUND OF THE INVENTION

The present invention relates in general to a thermal extensometer and pertains more particularly to a device for measuring deformations with an exceptionally high degree of resolution. The device of this invention is characterized by an inherent insensitivity of the device to temperature variations with the insensitivity being of the same order as the degree of resolution.

There are many types of devices available for measuring deformation but most are limited by poor stability, poor resolution, temperature sensitivity or limited operating temperature range. On the contrary, the device of the present invention is particularly suited to the measurement of very small minute temperature-induced deformations.

There are currently in existence a number of techniques and types of apparatus for measuring and determining thermal expansion. Some of these techniques require a material test sample of a special size and shape and employ a special heating oven equipped with a means of transmitting the thermal growth to a deflection sensing device operating at room temperature. The requirement for a special size and shape sample is inconvenient and sometimes difficult. The means of transmitting the thermal growth to a deflection sensing device operating at room temperature can introduce sensitivity, hysteresis and mechanical loading errors.

Another technique employs interferometric principles. This type of a measuring technique can measure very small deflections such as those occurring during material phase transformation. However, interferometric devices are usually expensive, complicated, fragile, not very portable and require inplane line-of-sight access between the heated sample under investigation and the deflection sensing optics or electronics. Also, heated air and optical windows used in conjunction with interferometric techniques cause diffraction and refraction of the light, resulting in troublesome errors.

In U.S. application Ser. No. 296,969, now abandoned there is shown a strain-measuring device that measures stress-induced strain while inherently cancelling thermal expansion strain. The thermal expansion strain cancellation is accomplished by fabricating the link from a material that has a thermal expansion characteristic that matches that of the specimen. On the other hand, in accordance with the principles of this invention the desire is not to measure stress-induced strain, but rather to measure expansion due to thermal variations.

The device of the present invention is inherently insensitive to temperature changes and is capable of operating in a vacuum and at extreme temperatures, including very high temperatures. The device of this invention is portable and attachable to the surface of a material without the requirement that the material be of any specific size or configuration. Therefore, one or more of the devices can be attached to sample coupons, fabricated parts, structures, structural components or mechanical equipment, and when attached to these parts or specimens is used to measure temperature induced deformations when the material to which it is attached changes temperature.

The use of the device of this invention generally falls into two categories. First, the device is used to measure minute deformations in deformation-sensitive structures like bridges, buildings and even spacecraft when they are subjected to cyclic or asymmetric heating. For example, the deformations taking place in a beam of a building or in a bridge span over a 24-hour period or even a one-year period can be continuously measured by the device and used to evaluate the design and operation of expansion joints.

Another category of practical use of the device of this invention is as a dilatometer for measuring the thermal expansion strain and determining the thermal coefficient of expansion of unstressed materials. Thermal expansion, or the thermal co-efficient of expansion is a basic physical property of materials. It is an important consideration in the design and function of mechanical equipment, optical devices, structures and other types of hardware. The applicability and high resolution of the device of this invention provides the opportunity to mount several units on a material sample and measure anisotropic thermal expansions simultaneously.

SUMMARY OF THE INVENTION

According to the invention, there is provided an extensometer for measuring thermally induced strain or expansion in a specimen which is subjected to temperature variations. The device of this invention basically comprises a link which can be provided in two sections. This link linearly spans the specimen in the direction and at the location in which the deformation is to be measured. The object of this invention is to make the thermal expansion of the link negligible over a broad and useful temperature range. The device also comprises a displacement sensor with high resolution and a broad temperature range such as a capacitance-based linear displacement sensor.

In accordance with one aspect of the present invention a material is selected that has a very low thermal coefficient of expansion. One such material is titanium silicate, another is vitreous quartz. In this way a relatively simple link construction can be used essentially employing a single link fixedly supported at one end and free at the other end with the motion detecting means supported at the free end of the link for detecting expansion of the specimen.

For some applications it may be desirable to further reduce the expansion of the link means to make the device further insensitive to thermal variations. Thus, in another embodiment of the invention the device comprises an elongated link means extending along the surface of the specimen and including two link sections comprised of a short section and a long section with the two link sections having different thermal expansion coefficients. The short section preferably has a higher coefficient of expansion than the long section and the particular coefficients are matched as a function of the length of each of the two link sections. Means are provided for supporting the short link section from the specimen with the short link extending in a first direction. Means are provided for securing the ends of each link section in fixed relationship with the long link section extending in a second direction that is opposite to the first direction. Motion detecting means which may comprise a capacitance sensor is disposed in cooperative relationship with the long link section and remote from the secured end of the long link section. A support means is provided for at least part of the motion detecting means for supporting the part from the specimen at a location spaced from the location of the short link supporting means. By selecting the short link section of a material having a relatively high coefficient of expansion in comparison with the long link section the resultant expansion of the two link sections tends to cancel and there is effectively no or negligible thermal expansion of the long link section at the motion detecting means. Therefore, it is only the expansion of the specimen by the motion detecting means that is being sensed.

In accordance with another embodiment of the present invention there is provided an elongated link extending along the surface of the specimen and supported at one end from the specimen. The elongated link is constructed of a material having a relatively low coefficient of thermal expansion. At least a portion of the motion detecting means is supported from another member which is in the form of a collar, which member has a relatively high coefficient of thermal expansion. This member is generally shorter in length than the length of the elongated link. This member is supported also from the specimen at a location spaced from the support for the link. This embodiment functions similarly to the previous embodiment in that the resultant expansion of the link and member provides essentially no or negligible effective expansion of the link relative to the motion detection means due to temperature variations.

BRIEF DESCRIPTION OF THE DRAWINGS

Numerous other objects, features and advantages of the invention should now become apparent upon a reading of the following detailed description taken in conjunction with the accompanying drawings, in which.

DETAILED DESCRIPTION

Figure 1:
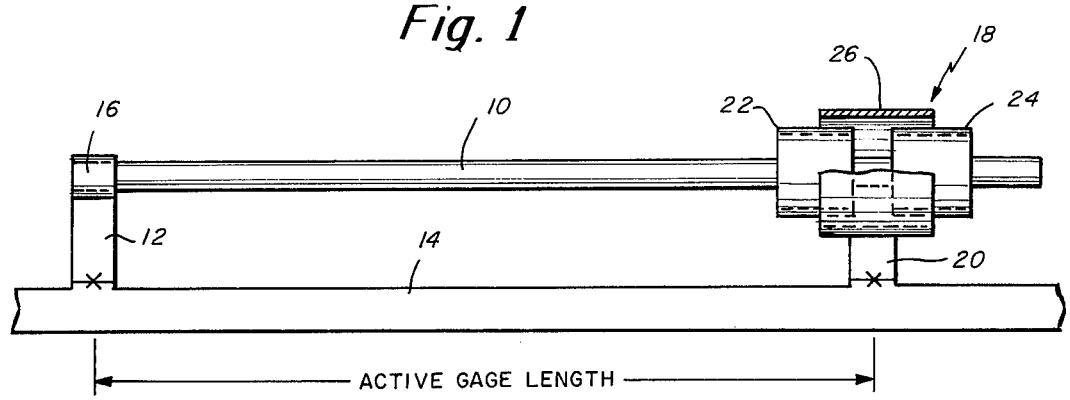
FIG. 1 is a schematic representation of one device constructed in accordance with the principles of the present invention.

FIG. 1 shows one device constructed in accordance with the present invention. The extensometer comprises an elongated link 10 which may be in the form of a cylindrically-shaped rod which is rigidly secured at one end by means of a bracket 12 elevated above the surface of the specimen 14. The bracket 12 is fixed to the surface of the specimen 14 by a convenient and suitable means, including commercially available high temperature cements, welds and the like. Bracket 12 includes a unitary sleeve 16 which functions as a receptacle for receiving therein one end of the link 10 which rigidly is coupled with the sleeve 16, and, therefore, rigidly secured to the specimen 14.

A motion detector 18 is positioned at the opposite end of the link 10 and receives this opposite end of the link. The detector 18 is also fixedly secured to the surface of the specimen 14 by means of a support bracket 20.

Thus, the link is rigidly attached to the specimen at one end and left relatively free (in the deformation-sensing direction) at its other end. The displacement sensor or detector 18 senses the relative linear motion between the free end of the link at a point on the specimen near the free end of the link. When the specimen is deformed, such as might result from a change in temperature that causes it to expand or contract, the effective length of the link will remain relatively constant and thus essentially only the deformation that has occurred in the specimen beneath the link will be sensed by the displacement detector. In the embodiment of FIG. 1 the link 10 is made relatively insensitive to thermal changes by selecting the link of a material with a very small thermal coefficient of expansion. One suitable material for the link 10 in this embodiment is vitreous quartz.

Figure 2:
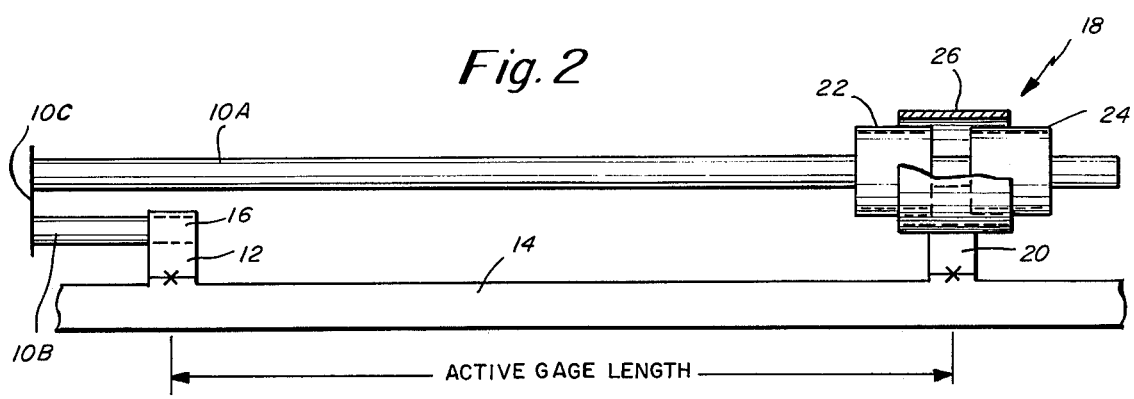
FIG. 2 shows a view in schematic fashion similar to that shown in FIG. 1 employing a two section link.
Figure 3:
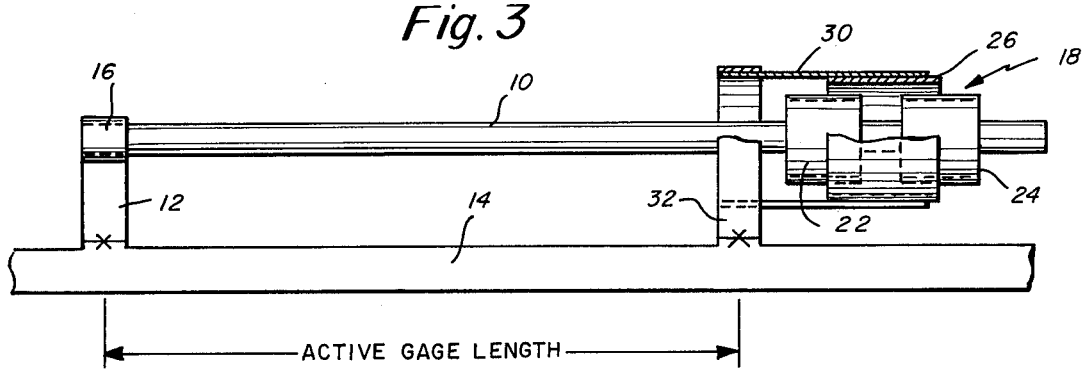
FIG. 3 shows another schematic representation of a further embodiment of the invention of a single link in combination with a support member.

FIGS. 1-3 all show essentially the same type of displacement sensor 18 which comprises a differential capacitor arrangement including one fixed capacitor plate and two moving capacitor plates with an air or vacuum dielectric between the fixed and moving plates. The capacitor plates in the drawings are actually shown in the form of cylinders including two smaller diameter cylinders 22 and 24 attached to, but electrically insulated from the free end of the link. These cylinders comprise the moving capacitor plates. The cylinders 22 and 24 may be mounted with the use of a suitable ceramic oxide collar which is disposed between the link and each cylinder. The detector 18 also comprises a hollow cylinder 26 with an inside diameter slightly larger than the outside diameters of the moving capacitor cylinders 22 and 24. Cylinder 26 forms the fixed plate of the capacitor sensor. The two moving cylinders are positioned so that they are concentric with the fixed capacitor cylinder and separated axially from each other in such a manner that both of the smaller cylinders extend into the hole through the fixed cylinder in a position like that shown in the drawings.

The fixed capacitor cylinder 26 is attached to, but electrically insulated from, the frame or bracket 20 which is attached to the specimen near the free end of the link. The deformation occurring in the specimen between the points of attachment of the brackets 12 and 20 causes one of the moving capacitor cylinders to move further into the hole of the fixed capacitor cylinder while the other moving capacitor cylinder moves in a direction out of the fixed capacitor cylinder hole. In this manner the capacitance between one moving capacitor cylinder and the fixed capacitor cylinder increases while the capacitance between the other moving capacitor cylinder and the fixed capacitor cylinder decreases. The two effective capacitors may then be connected as one half of a bridge circuit to produce an electrical analog signal indicative of the specimen deformation. The connection to the bridge circuit and the producing of the analog signal is not shown herein as these are well known techniques.

As previously mentioned, in the first embodiment shown in FIG. 1 the link 10 is made insensitive to thermal changes by being constructed of a material having a very low coefficient of expansion. In this way, when the specimen 14 expands it is essentially only this expansion that is sensed by the motion detector 18. However, where even a slight expansion of the link is a concern further correction can be provided by the embodiments shown in FIGS. 2 and 3.

In the drawings like reference characters are used to identify like parts throughout. Thus, in FIG. 2 there is shown the specimen 14, the motion detector 18, and the support brackets 12 and 20. The link is constructed in two sections 10A and 10B which are interconnected by means of a securing member 10C. Securing member 10C may be a plate or disc that is securely fastened to one end of each of the link sections 10A and 10B. The other end of link section 10B is supported in the bracket 16 in a manner similar to that shown in FIG. 1. However, the link 10B extends in a direction away from the motion detector 18. The link 10A extends back over the bracket 12 to a spaced point over the specimen in the area of bracket 20. In the embodiment shown in FIG. 2 and in the other two embodiments disclosed herein there may be provided additional supports for the link 10 or link section 10A so that the link is properly supported therealong. For example, in FIG. 2 the link section 10A may be supported at its extreme free end by suitable supporting structure.

In FIG. 2 the link sections have significantly different thermal expansion coefficients. The thermal expansion coefficient of section 10B is much larger than that of section 10A so that upon a change in temperture, the total expansion from end to end of section 10B will be equal to the total expansion of section 10A. In this way the effective length of the link remains constant with temperature. For example, if the link section 10A is four times as long as the link section 10B then the coefficients of expansion for the two sections would be selected to be in the same ratio so as to provide a cumulative expansion that is essentially zero between the brackets 12 and 20. In FIG. 2 the link section 10A may be made of aluminum oxide of 1.75 inch length while the link section 10B is of 300 series stainless steel of 0.75 inch length. The active gauge length is 1.0 inch.

FIG. 3 shows still another alternative embodiment of this invention which comprises the link 10 supported from the bracket 12 as in the embodiment of FIG. 1. In FIG. 3 the displacement sensor 18 is offset from a position directly above a specimen attachment point. The sensor is held in this offset position by means of a support collar 30 supported from a support bracket 32. As in the embodiment of FIG. 2, the thermal expansion coefficient of collar 30 is much larger than that of the link 10 so that after a change in temperature the total expansion of the collar 30 is equal to the total expansion of the link 10 and thus the effective length of the link remains constant with temperature. For example, as the temperature increases the link 10 tends to move to the right in FIG. 3. However, the collar 30 is also effected and moves in the same direction and essentially at the same rate with temperature so that there is in effect no link movement with temperature. The collar 30 and link 10 of FIG. 3 may be constructed of the same material as mentioned with regard to FIG. 2.

Having described a limited number of embodiments of the present invention it should now become apparent to those skilled in the art that numerous modifications can be made therein all of which are contemplated as falling within the scope of this invention. For example, the members can be made of many different types of materials. For example, in the embodiments of FIGS. 2 and 3 the link sections or the link and frame member can be constructed of materials having different coefficients of thermal expansion. However, in accordance with the invention it is desired to match these members so as to provide a resultant expansion that is essentially zero or very negligible.

What is claimed is:

1. A thermal extensometer for measuring thermally induced strain or expansion in a specimen subjected to thermal variations, said extensometer comprising;
   an elongated link extending along the surface of said specimen and including two link sections including a short section and a long section with the two link sections having different thermal expansion coefficients to thereby provide a total expansion between sections that is negligible,
   means securing one end of each link section in fixed relationship,
   means for supporting the other end of the short link section from the specimen,
   motion detecting means disposed in cooperative relationship with the long link section adjacent the other end thereof,
   and means for supporting at least part of the motion detecting means from the specimen at a location spaced from the location of the short link supporting means.

2. A thermal extensometer as set forth in claim 1 wherein said motion detecting means comprises two movable cylinders and one fixed cylinder.

3. A thermal extensometer as set forth in claim 2 wherein said means for supporting at least part of the motion detecting means comprises means for supporting the fixed cylinder.

4. A thermal extensometer as set forth in claim 1 wherein the short link section has a higher expansion coefficient than the long link section.

5. A thermal extensometer as set forth in claim 4 wherein the lengths of the link sections is in the reciprocal ratio as the coefficients of expansion of the sections.

6. A thermal extensometer for measuring thermally induced strain or expansion in a specimen subjected to thermal variations, said extensometer comprising;
   an elongated link extending along the surface of said specimen, means for supporting one end of the link,
   motion detecting means disposed in cooperative relationship adjacent the other end of the link,
   and means for supporting at least a part of the motion detecting means including a frame member extending in the same direction as the link,
   said link and frame member having different thermal expansion coefficients to thereby provide matching expansions or contractions between link and frame member.

7. A thermal extensometer as set forth in claim 6 wherein the frame member has a higher expansion coefficient than the link.

8. A thermal extensometer as set forth in claim 7 wherein the lengths of the link and frame member are in the reciprocal ratio as the coefficients of expansion of the link and frame member.

9. A thermal extensometer as set forth in claim 6 wherein said supporting means for the motion detecting means comprises a bracket attached to the specimen.

10. A thermal extensometer as set forth in claim 9 wherein the frame member comprises a collar for supporting a fixed capacitor cylinder, said collar extending from the side of the bracket.

11. A thermal extensometer as set forth in claim 1 wherein said motion detecting means comprises a differential capacitive linear displacement sensor.

12. A thermal extensometer as set forth in claim 11 wherein said means of detecting motion comprises movable and fixed cylinders operating in a coaxial relationship with each other to form the differential capacitive linear displacement sensor.

13. A thermal extensometer as set forth in claim 6 wherein said motion detecting means comprises a differential capacitive linear displacement sensor.

14. A thermal extensometer as set forth in claim 13 wherein said means of detecting motion comprises movable and fixed cylinders operating in a coaxial relationship with each other to form the differential capacitive linear displacement sensor.

* * * * *